United States Patent [19]

Nakagawa et al.

[11] Patent Number: 4,883,868
[45] Date of Patent: Nov. 28, 1989

[54] 7-AMINO-3-(SUBSTITUTED ISOINDOLINIUM)METHYL-3-CEPHEM DERIVATIVES

[75] Inventors: Susumu Nakagawa; Ryosuke Ushijima; Fumio Nakano; Koji Yamada, all of Okazaki; Eiichi Mano, Kariya, all of Japan

[73] Assignee: Banyu Pharmaceutical Co., Ltd., Tokyo, Japan

[21] Appl. No.: 64,462

[22] Filed: Jun. 22, 1987

Related U.S. Application Data

[63] Continuation-in-part of Ser. No. 813,614, Dec. 26, 1985, Pat. No. 4,677,100.

[30] Foreign Application Priority Data

Dec. 27, 1984 [JP] Japan .................. 59-273591
Aug. 6, 1985 [JP] Japan .................. 60-171839
Dec. 9, 1986 [JP] Japan .................. 61-291431

[51] Int. Cl.⁴ .................. C07D 501/46; A61K 31/545
[52] U.S. Cl. .................. 540/222
[58] Field of Search .................. 514/202; 540/222

[56] References Cited

U.S. PATENT DOCUMENTS

| | | | |
|---|---|---|---|
| 4,406,899 | 9/1983 | Aburaki | 540/222 |
| 4,457,929 | 7/1984 | Kamachi | 514/202 |
| 4,525,473 | 6/1985 | Aburaki | 540/222 |
| 4,632,918 | 12/1980 | Angerbauer | 514/202 |
| 4,677,100 | 6/1987 | Nakagawa | 540/222 |

OTHER PUBLICATIONS

Burger, A., *Medicinal Chemistry*, 2nd ed. (1960, Interscience Publishers, Inc.: New York), pp. 42–43.
McOmie, J., *Protective Groups in Organic Chemistry*, (1973, Plenum Press: New York), pp. 46–67, 157, 171–175.

Primary Examiner—Nicholas S. Rizzo
Attorney, Agent, or Firm—Oblon, Spivak, McClelland, Maier & Neustadt

[57] ABSTRACT

A compound having the formula:

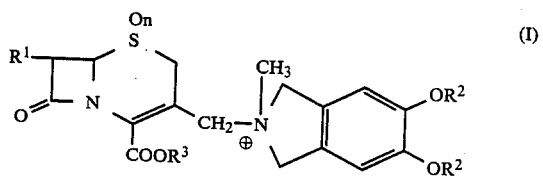

wherein $R^1$ is an amino group or a protected amino group, $R^2$ is a hydrogen atom or a protecting group for a hydroxyl group, $R^3$ represents negative charge, a hydrogen atom or a protecting group for a carboxyl group, and n is 0 or 1, and a salt thereof.

10 Claims, No Drawings

7-AMINO-3-(SUBSTITUTED ISOINDOLINIUM)METHYL-3-CEPHEM DERIVATIVES

This application is continuation in part of U.S. patent application Ser. No. 06/813,614 filed on Dec. 26, 1985, now 4,677,100.

BACKGROUND OF THE INVENTION

1. Field of the Invention

The present invention relates to novel intermediates useful for the production of cephalosporin derivatives which are useful in the pharmaceutical fields, and a process for the production of the intermediates.

2. Discussion of Background

Since β-lactam antibiotics exhibit selective toxicity only against bacteria and present no substantial effects against animal cells, they have performed important roles as antibiotics with no substantial side effects in the prevention or treatment of diseases caused by the infection of bacteria.

Particularly, cephalosporin derivatives are generally stable against penicillinase and have a broad antibacterial spectrum, and thus they are frequently employed for the prevention and treatment of diseases caused by the infection of bacteria.

On the other hand, however, a cephalosporin derivative having a more potent and broader antibacterial spectrum is desired in that few existing cephalosporins are adequately active for the curing of obstinate infectious diseases caused by resistant Staphylococci, or glucose non-fermentative Gram-negative rods such as resistant Pseudomonas aeruginosa, or Acinetobacter calcoaceticus which have various resistant mechanisms.

Under the circumstances, the present inventors have conducted extensive researches on cephalosporin derivatives, and as a result, have found that a group of cephalosporin derivatives having an isoindolinium methyl group substituted by two hydroxyl groups at adjacent positions, introduced at the 3-position of the cephem nucleus, exhibit remarkably strong antibacterial activities against Gram-negative bacteria, particularly against glucose non-fermentative Gram-negative rods such as Pseudomonas aeruginosa, Pseudomonas cepacia and the like (Japanese patent application No. 292183/1985).

SUMMARY OF THE INVENTION

It is an object of the present invention to provide a novel intermediate useful for the production of the cephalosporin derivatives having excellent antibacterial activities, as disclosed in Japanese patent application No. 292183/1985, and to provide a process for the production of the intermediate.

As a result of extensive researches on the industrial process for the production of such cephalosporin derivatives, the present inventors have found that a cephalosporin derivative represented by the general formula I given hereinafter, is a useful and important intermediate for the preparation of the cephalosporin derivatives having excellent antibacterial activities as disclosed in Japanese patent application No. 292183/1985. The present invention has been accomplished on the basis of this discovery.

The present invention provides a compound having the formula:

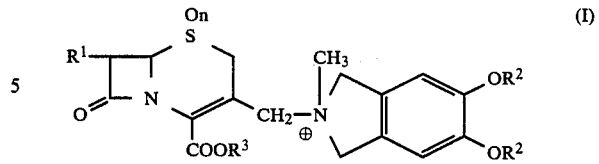

wherein $R^1$ is an amino group or a protected amino group, $R^2$ is a hydrogen atom or a protecting group for a hydroxyl group, $R^3$ represents a negative charge, a hydrogen atom or a protecting group for a carboxyl group, and n is 0 or 1, and a salt thereof.

DETAILED DESCRIPTION OF THE PREFERRED EMBODIMENTS

Now, definitions of various terms used in this specification will be explained with reference to certain examples.

The protected amino group means an amino group protected by a protecting group known as an amino-protecting group, such as an aralkyl group such as a benzyl group, a trityl group or a diphenylmethyl group; a substituted phenylthio group such as an o-nitrophenylthio group; an aralkylidene group such as a p-chlorobenzylidene group, a p-nitrobenzylidene group, an α-naphthylidene group, a β-naphthylidene group, a salicylidene group or a benzylidene group; a substituted alkylidene group such as 1-methoxycarbonyl-2-propylidene group; a substituted cycloalkylidene group such as a 2-ethoxycarbonylcyclohexylidene group; a lower alkanoyl group such as a formyl group, an acetyl group, a butyryl group, an oxalyl group, a succinyl group or a pivaloyl group; a lower alkoxycarbonyl group such as a methoxycarbonyl group, an ethoxycarbonyl group, a propoxycarbonyl group, a butoxycarbonyl group, a tert-butoxycarbonyl group, an isobutoxycarbonyl group, a pentyloxycarbonyl group, a hexyloxycarbonyl group or a 1-cyclopropylethoxycarbonyl group; an arylalkanoyl group such as a phenylacetyl group or a phenoxyacetyl group; an aralkyloxycarbonyl group such as a benzyloxycarbonyl group, a p-nitrobenzyloxycarbonyl group or a phenethyloxycarbonyl group; or a halo-lower alkanoyl group such as a chloroacetyl group, a dichloroacetyl group, a trifluoroacetyl group or a trichloroacetyl group.

The protecting group for a carboxyl group means a protecting group for a carboxyl group which can readily be removed by acid treatment, such as a lower alkyl group such as a tert-butyl group; a haloalkyl group such as a 2,2,2-trichloroethyl group or a 2,2,2-trifluoroethyl group; a lower alkanoyloxyalkyl group such as an acetoxymethyl group, a propionyloxymethyl group, a 1-acetoxyethyl group or a 1-propionyloxyethyl group; a lower alkoxycarbonyloxyalkyl group such as a 1-(ethoxycarbonyloxy)ethyl group or a 1-(methoxycarbonyloxy)ethyl group; an aralkyl group such as a benzyl group, a 4-methoxybenzyl group, a 4-nitrobenzyl group, a phenethyl group, a trityl group, a benzhydryl group, a bis(4-methoxyphenyl)methyl group or a 3,4-dimethoxybenzyl group; or a lower alkylsilyl group such as a trimethylsilyl group or a tert-butyldimethylsilyl group.

The protecting group for a hydroxyl group means a conventional protecting group for a hydroxyl group which can readily be removed, such as a 2-methoxyethoxymethyl group, a methoxymethyl group, a methylthiomethyl group, a tetrahydropyranyl group, a phenacyl group, an isopropyl group, a tert-butyl group, a benzyl group, a 4-nitrobenzyl group, an acetyl group, a 2,2,2-trichloroethoxycarbonyl group, a benzyloxycarbonyl group, an acetonide group, a trimethylsilyl group or a tert-butyldimethylsilyl group.

$R^3$ being negative charge means that the carboxyl group forms an intramolecular salt with the isoindolinium group.

Now, a process for the production of the compound of the present invention will be described.

The compound of the present invention can be prepared by reacting a compound having the formula:

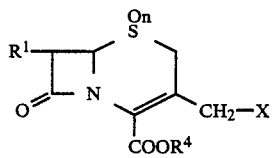

wherein $R^1$ and n are as defined above, $R^4$ is a hydrogen atom or a protecting group for a carboxyl group, and X is a leaving group, or a salt thereof, with a compound having the formula:

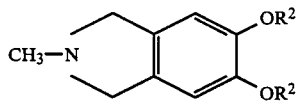

wherein $R^2$ is as defined above, or a salt thereof, to obtain a compound having the formula:

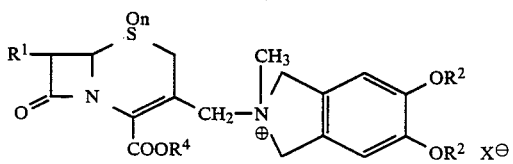

wherein $R^1$, $R^2$, $R^4$ and n are as defined above, and $X^\ominus$ is an anion, and if necessary, reducing the sulfoxide group of the compound of the formula II when n is 1, removing the protecting group, and/or converting the compound of the formula II to an intramolecular salt or to another salt.

The compound of the formula IV used as the starting material of the compound of the present invention, can be prepared, for instance, by a method disclosed in the Journal of Antibiotics, Vol. 38, p. 1738-1751 (1985). Here, the sulfoxide of the compound of the formula IV, can be prepared by a conventional method as disclosed in Japanese Unexamined Patent Publication No. 10099/1973, for example, by treating the compound of the formula IV wherein n=0, with an oxidizing agent such as m-chloroperbenzoic acid or peracetic acid in an organic solvent such as methylene chloride under cooling with ice.

The compound of the formula III as another starting material for the compound of the present invention, can be prepared by firstly producing the compound wherein $R^2$ is a hydrogen atom in accordance with a method as disclosed in Japanese patent applications No. 275196/1985, No. 275197/1985 and No. 283080/1985, and then producing the compound of the formula III wherein $R^2$ is a protecting group for a hydroxyl group, by a conventional method for introducing a protecting group to a hydroxyl group, for example, in accordance with a method as disclosed in "Protective Groups in Organic Synthesis" published by Wiley Company in 1981, or "Protective Groups in Organic Chemistry" edited by J. F. W. McOmie and published by Plenum Press Company in 1973.

The process for producing the compound of the formula II by reacting the compound of the formula III to the compound of the formula IV, can be conducted in an anhydrous organic solvent such as methylene chloride, chloroform, ethyl ether, ethyl acetate, butyl acetate, tetrahydrofuran, acetonitrile, N,N-dimethylformamide, dimethylsulfoxide or a solvent mixture thereof by using from 1 to 2 mols of the compound of the formula III relative to 1 mol of the compound of the formula IV, at a temperature of from 0 to 35° C. for from 0.5 to 5 hours. When a salt of the compound of the formula III, such as the hydrochloride, the hydrobromide, the sulfate or the acetate, is used for this process, it is necessary to add a tertiary amine such as triethylamine, N-methylmorpholine or N,N-dimethylaniline, in an amount required for neutralization. The compound of the formula III may be silylated in the above solvent with a silylating agent such as N,O-bis(trimethylsilyl)acetamide, and may be used in the silylated form.

Substituent X in the compound of the formula IV is a leaving group such as a chlorine atom, a bromine atom, an iodine atom, an acetoxy group, a trifluoroacetyloxy group, a methanesulfonyloxy group, a phenylsulfonyloxy group, a trifluoromethanesulfonyloxy group or a p-toluenesulfonyloxy group. In a case where the leaving group X is an acetoxy group, the above process can be conducted even in a solvent mixture of the above organic solvent with water, in water or in a substantially neutral aqueous solution such as a phosphate buffer solution, if necessary in the presence of a thiocyanate such as potassium thiocyanate or sodium thiocyanate, an iodide such as sodium iodide or a reaction accelerator such as a phasetransfer catalyst. Further, a compound of the formula IV wherein the leaving group X is an iodine atom, can be prepared by reacting a compound of the formula IV wherein the leaving group X is a chlorine atom, with an iodide such as sodium iodide in a solvent such as acetone or N,N-dimethylformamide, or by reacting a compound of the formula IV wherein X is an acetoxy group, with trimethylsilyl iodide in a solvent such as methylene chloride, chloroform, diethyl ether, ethyl acetate, butyl acetate, tetrahydrofuran, acetonitrile, N,N-dimethylformamide, dimethylsulfoxide or a mixture thereof.

The isolation and purification of the compound of the formula II from the reaction solution thus obtained, can be conducted by conventional means such as concentration, solvent extraction, recrystallization, chromatography, etc. Further, when a protecting group is present in the compound of the formula II as the reaction product, the reaction solution may be subjected to a step for removing the protecting group, as it is or in a crude product form.

The step for removing the protecting group can be conducted by selecting a suitable conventional method depending upon the type of the protecting group. For example, the protecting groups for an amino group, a hydroxyl group and a carboxyl group can be removed by the treatment with an acid such as formic acid, hydrochloric acid, trifluoroacetic acid, benzenesulfonic acid, p-toluenesulfonic acid or a mixture thereof in an inert solvent such as methylene chloride, ethylene chloride, benzene or a solvent mixture thereof. When trifluoroacetic acid is used, it is preferred to add anisole as a reaction accelerator. For this step of removing a protecting group, the reaction temperature is not particularly limited, and may suitably be selected depending upon the starting compound, the chemical nature of the reaction product, the type of the protecting group and the type of the method for the removal.

In the compound of the formula II, when the amino group as $R^1$ is protected by a phenylacetyl group or a phenoxyacetyl group, such a protecting group can be removed in accordance with a method disclosed in Japanese Examined Patent Publication No. 20319/1974.

For example, such a compound of the formula II is reacted with phosphorous pentachloride or phosphorous oxychloride in a solvent such as benzene, toluene, ethyl acetate, methylene chloride, ethylene chloride or a mixture thereof in the presence of an acid binding agent such as pyridine, triethylamine, sodium hydrogencarbonate or potassium hydrogencarbonate at a temperature of from $-80°$ C. to $50°$ C., preferably from $-65°$ C. to $0°$ C. for from 0.5 to 2 hours, and then treated with a lower alcohol such as methanol, ethanol or propanol, followed by hydrolysis, whereby the amino-protecting group can be removed. In such a case, $R^2$ in the compound of the formula II is preferably a protecting group for a hydroxyl group.

Further, the removal of the phenylacetyl group or the phenoxyacetyl group can also be conducted by a method as disclosed in Japanese Unexamined Patent Publication No. 255795/1985, i.e. by using penicillin G amidase or fixed penicillin G amidase at a pH of from 7 to 8, preferably from 7.5 to 7.8, in water or in a solvent mixture of water and a polar organic solvent such as acetonitrile, ethanol or tetrahydrofuran, at room temperature. This reaction is preferably conducted by maintaining the pH at a constant level by an addition of a base such as lithium hydroxide, sodium hydroxide, potassium hydroxide, triethylamine tripropylamine or pyridine.

In the compound of the formula II, when a sulfoxide is present, such a sulfoxide may be reduced by a conventional method, for example, in accordance with the description in Journal of Organic Chemistry, Vol. 35, p. 2430 (1970). Namely, the reduction can be conducted by dissolving the compound of the formula II in an inert organic solvent such as acetone, methylene chloride, chloroform, tetrahydrofuran or ethyl acetate, then adding sodium iodide or potassium iodide and acetyl chloride thereto and conducting the reaction at a temperature of from $-40°$ C. to $0°$ C. for from 1 to 2 hours.

From the reaction solution obtained in the above-mentioned steps, the desired compound of the present invention may be obtained by a method per se known, such as concentration, solvent extraction, recrystallization or chromatography, in the form of an intramolecular salt or its solvate, or in the form of an acid addition salt with an acid such as hydrochloric acid, hydrobromic acid, hydroiodic acid, phosphoric acid, sulfuric acid, nitric acid, acetic acid, oxalic acid or trifluoroacetic acid, or its solvate. Here, the solvate may be a solvate with e.g. water, methanol or ethanol.

The following compounds may be mentioned as Examples of the desired compounds of the present invention:

7-Amino-3-(5,6-dihydroxy-2-methyl-2-isoindolinium)-methyl-3-cephem-4-carboxylate 7-Amino-3-(5,6-dihydroxy-2-methyl-2-isoindolinium)-methyl-3-cephem-4-carboxylate hydrochloride 7-Amino-3-(5,6-dihydroxy-2-methyl-2-isoindolinium)-methyl-3-cephem-4-carboxylate dihydrochloride 7-Amino-3-(5,6-dihydroxy-2-methyl-2-isoindolinium)-methyl-3-cephem-4-carboxylate hydroiodide 7-Amino-3-(5,6-dihydroxy-2-methyl-2-isoindolinium)-methyl-3-cephem-4-carboxylate hydrobromide p-Methoxybenzyl 7-benzylideneamino-3-[5,6-di(trimethylsilyloxy)-2-methyl-2-isoindolinium]methyl-3-cephem-4-carboxylate iodide Benzhydryl 7-benzylideneamino-3-[5,6-di(trimethylsilyloxy)-2-methyl-2-isoindolinium]methyl-3-cephem-4-carboxylate iodide p-Methoxybenzyl 7-formamido-3-[5,6-dihydroxy-2-methyl-2-isoindolinium]methyl-3-cephem-4-carboxylate iodide 7-Phenylacetamido-3-(5,6-dihydroxy-2-methyl-2-isoindolinium)methyl-3-cephem-4-carboxylate Now, the present invention will be described in further detail with reference to Examples and Reference Examples. However, it should be understood that the present invention is by no means restricted to these specific Examples.

REFERENCE EXAMPLE 1 p-Methoxybenzyl 7-benzylideneamino-3-chloromethyl-3-cephem-4-carboxylate 1.72 g (4.4 mM) of p-methoxybenzyl 7-amino-3-chloromethyl-3-cephem-4-carboxylate hydrochloride was suspended in a mixture comprising 16 ml of ethyl acetate and 6 ml of water. Then, 8 ml of a 1N sodium hydroxide aqueous solution was added thereto, and the mixture was stirred for 15 minutes. The organic layer was separated, and washed with a saturated sodium chloride aqueous solution. Then, 10 g of anhydrous magnesium sulfate and 0.54 ml (5.3 mM) of benzaldehyde were added in this order, and the mixture was stirred for 2 hours. The reaction solution thus obtained was filtered to remove insolubles, and the solvent was distilled off under reduced pressure to obtain 1.8 g (yield: 89.5%) of p-methoxybenzyl 7-benzylideneamino-3-chloromethyl-3-cephem-4-carboxylate.

m.p.: 124° C.

IR(KBr)cm$^{-1}$: 1770, 1710, 1640, 1520, 1360, 1250

NMR(CDCl$_3$) δ ppm: 3.30 and 3.66(2H,ABq,J=18 Hz), 3.70(3H,s), 4.30 and 4.60(2H,ABq,
J=12Hz), 5.03(1H,d,J=4.5 Hz),
5.20(2H,s), 5.25(1H,dd,J=4.5 and
1.5 Hz), 6.80–7.70(9H,m),
8.50(1H,d,J=1.5 Hz)

REFERENCE EXAMPLE 2 p-Methoxybenzyl 7-benzylideneamino-3-iodomethyl-3-cephem-4-carboxylate 30 g (65.65 mM) of p-methoxybenzyl 7-benzylideneamino-3-chloromethyl-3-cephem-4-carboxylate was dissolved in 500 ml of acetone. Then, 29.5 g (197 mM) of sodium iodide was added thereto, and the mixture was stirred at room temperature for 1 hour. From the reaction solution thus obtained, the solvent was distilled off under reduced pressure. To the residue, 500 ml of ethyl acetate was added. The mixture was washed with a saturated sodium thiosulfate aqueous solution and then with a saturated sodium chloride aqueous solution, then dried over anhydrous sodium sulfate. Then, the solvent was distilled off under reduced pressure to obtain 27 g (yield: 75%) of p-methoxybenzyl 7-benzylideneamino-3-iodomethyl-3-cephem-4-carboxylate.

m.p.: 113° C.
IR(KBr)cm$^{-1}$: 1770, 1720, 1630, 1610, 1520, 1360, 1240
NMR(CDCl$_3$) δ ppm: 3.36 and 3.76(2H,ABq,J=18 Hz),
3.80(3H,s), 4.32(2H,br s),
5.06(1H,d,J=4.5 Hz), 5.23(2H,s),
5.30(1H,d,J=4.5 Hz), 6.80–7.70
(9H,m), 8.52(1H,s)

REFERENCE EXAMPLE 3

7-Amino-3-iodomethyl-3-cephem-4-carboxylic acid hydrochloride 3.25 g (59.3 mM) of p-methoxybenzyl 7-benzylideneamino-3-iodomethyl-3-cephem-4-carboxylate was dissolved in 55 ml of 99% formic acid. Under cooling with ice, 23 ml of concentrated hydrochloric acid was added to this solution, and the mixture was stirred at room temperature for 1.5 hours. To the reaction solution, 200 ml of acetone and 400 ml of isopropyl ether were added. Precipitates were collected by filtration, washed with acetone and dried to obtain 12 g (yield: 53.7%) of 7-amino-3-iodomethyl-3-cephem-4-carboxylic acid hydrochloride.

IR(KBr)cm$^{-1}$: 1800, 1620, 1400, 1350
NMR(DMSO-d$_6$/D$_2$O) δ ppm: 3.70(2H,s), 4.55(2H,s),
5.10(1H,d,J=4.5 Hz),
5.23(1H,d,J=4.5 Hz)

REFERENCE EXAMPLE 4 p-Methoxybenzyl 3-chloromethyl-7-formamido-3-cephem-4-carboxylate

To 15 g (37 mM) of p-methoxybenzyl 7-amino-3-chloromethyl-3-cephem-4-carboxylate hydrochloride, 500 ml of ethyl acetate and 100 ml of water were added. Under cooling with ice, the mixture was adjusted to pH 7.5 with a 1N sodium hydroxide aqueous solution and dissolved. The organic layer was separated, washed with a saturated sodium chloride aqueous solution, and then concentrated under reduced pressure. The oily residue was dissolved in 150 ml of methylene chloride. To this solution, a mixed anhydride solution prepared from 4.8 ml (127 mM) of 99% formic acid and 12 ml (127 mM) of acetic anhydride, was dropwise added under cooling with ice, and the mixture was stirred for 2 hours. The reaction solution was concentrated under reduced pressure. To the residue, 300 ml of ethyl acetate, 300 ml of tetrahydrofuran and 100 ml of water were added, and the mixture was adjusted to pH 7.5 with a 1N sodium hydroxide aqueous solution. The organic layer was separated, and washed with a saturated sodium chloride aqueous solution. The organic layer was dried over anhydrous sodium sulfate, and concentrated under reduced pressure to obtain 14.5 g (yield: 99%) of p-methoxybenzyl 3-chloromethyl-7-formamido-3-cephem-4-carboxylate.

IR(KBr)cm$^{-1}$: 1780, 1720, 1650, 1610, 1520, 1380
NMR(DMSO-d$_6$) δ ppm: 3.63(2H,m), 3.75(3H,s), 4.48(2H,s),
5.15(1H,d,J=4.5 Hz), 5.20(2H,s),
5.80(1H,dd,J=4.5 and 9 Hz),
6.90(2H,d,J=9 Hz), 7.33(2H,d,J=9 Hz),
8.10(1H,s), 9.10(1H,d,J=9Hz)

REFERENCE EXAMPLE 5 p-methoxybenzyl 7-formamido-3-iodomethyl-3-cephem-4-carboxylate 14.5 g (36.6 mM) of p-methoxybenzyl 3-chloromethyl-7-formamido-3-cephem-4-carboxylate was dissolved in 360 ml of acetone. Under cooling with ice, 13.7 g (91.4 mM) of sodium iodide was added to this solution, and the mixture was stirred for 30 minutes, and further at room temperature for 30 minutes. The reaction solution was concentrated under reduced pressure, and the oily residue was dissolved by an addition of ethyl acetate. The organic layer was washed sequentially with water, a saturated sodium thiosulfate aqueous solution and a saturated sodium chloride aqueous solution. The extract was dried over anhydrous sodium sulfate, and concentrated under reduced pressure. The oily residue was subjected to silica gel column chromatography (Wakogel C-300, eluted with 20% ethyl acetate-chloroform), and the fraction containing the desired product was concentrated to obtain 15.7 g (yield: 87.9%) of p-methoxybenzyl 7-formamido-3-iodomethyl-3-cephem-4-carboxylate.

IR(KBr)cm$^{-1}$: 1780, 1720, 1650, 1620, 1520, 1240
NMR(DMSO-d$_6$) δ ppm: 3.65(2H,m), 3.71(3H,s), 4.33(2H,s),
5.10(1H,d,J=4.5 Hz), 5.17(2H,s),
5.70(1H,dd,J=4.5 and 9 Hz),
6.88(2H,d,J=9Hz), 7.30(2H,d,J=9 Hz),
8.07(1H,s), 8.97(1H,d,J=9 Hz)

EXAMPLE 1 p-Methoxybenzyl 7-benzylideneamino-3-[5,6-di(trimethylsilyloxy)-2-methyl-2-isoindolinium]methyl-3-cephem-4-carboxylate iodide 541 mg (2.2 mM) of 5,6-dihydroxy-2-methylisoindoline hydrobromide was suspended in 5 ml of dried ethyl acetate. Then, 0.32 ml (2.31 mM) of triethylamine and 1.1 ml (4.45 mM) of N,O-bis(trimethylsilyl)acetamide were added thereto, and the mixture was stirred for 1 hour. From the reaction solution thus obtained, insolubles were removed by filtration, and the filtrate thus obtained was added to 5 ml of a dried ethyl acetate solution containing 1.156 g (2 mM) of p-methoxybenzyl 7-benzylideneamino-3-iodomethyl-3-cephem-4-carboxylate, and the mixture was stirred for 30 minutes. This reaction solution is poured into 70 ml of isopropyl ether. Precipitates thereby formed were collected by filtration and dried under reduced pressure to obtain 1.3 g (yield: 75.8%) of p-methoxybenzyl 7-benzylideneamino-3-[5,6-di(trimethylsilyloxy)-2-methyl-2-isoindolinium]methyl-3-cephem-4-carboxylate iodide.

IR(KBr)cm$^{-1}$: 1780, 1720, 1610, 1510, 1350, 1250
NMR(DMSO-d$_6$) δ ppm: 0.25(18H,s), 3.15(3H,br s),
3.30(2H,br s), 3.70(3H,s),
4.40(2H,br s), 4.60(2H,m),
4.75(2H,m), 5.10(1H,d,J=4.5 Hz),
5.20(2H,s), 5.40(1H,d,J=4.5 Hz),
6.90–7.80(9H,m), 8.56(1H,s)

EXAMPLE 2

7-Amino-3-(5,6-dihydroxy-2-methyl-2-isoindolinium)-methyl-3-cephem-4-carboxylate hydrochloride 1.3 g (1.15 mM) of p-methoxybenzyl 7-benzylideneamino-3-[5,6-di(trimethylsilyloxy)-2-methyl-2-isoindolinium]methyl-3-cephem-4-carboxylate iodide was dissolved in 2.6 ml of 99% formic acid. Then, 1.3 ml of concentrated hydrochloric acid was added thereto, and the mixture was stirred for 1 hour. The reaction solution thus obtained was poured into 50 ml of acetone. Precipitates thereby formed were collected by filtration, and dissolved in a mixture comprising 1 ml of water and 1 ml of acetone. To this solution, 50 ml of acetone was added. Precipitates thereby formed were collected by filtration, and dried under reduced pressure to obtain 514 mg (yield: 75.4%) of 7-amino-3-(5,6-dihydroxy-2-methyl-2-isoindolinium)methyl-3-cephem-4-carboxylate hydrochloride.

m.p.: 180° C. (decomposed)
IR(KBR)cm$^{-1}$: 3400, 1790, 1620, 1335
NMR(DMSO-d$_6$/CF$_3$COOH) δ ppm: 3.15(3H,br s), 3.70–4.20(2H,q), 4.50(2H,m),
4.63(2H,br s), 4.80(2H,m),
5.05(1H,d,J=4.5 Hz),
5.30(1H,d,J=4.5 Hz), 6.85(2H,s)

EXAMPLE 3

Benzyhydryl 7-benzylideneamino-3-[5,6-di(trimethylsilyloxy)-2-methyl-2-isoindolinium]methyl-3-cephem-4-carboxylate iodide 777 mg (1.54 mM) of benzyhydryl 7-benzylideneamino-3-chloromethyl-3-cephem-4-carboxylate was dissolved in 16 ml of acetone. Then, 692 mg (4.62 mM) of sodium iodide was added thereto, and the mixture was stirred for 1 hour. From the reaction solution thus obtained, the solvent was distilled off under reduced pressure. Then, 30 ml of ethyl acetate was added to the residue, and the mixture was washed with a saturated sodium thiosulfate aqueous solution and a saturated sodium chloride aqueous solution. The extract was dried over anhydrous sodium sulfate, and filtered to obtain an ethyl acetate solution containing the 3-iodomethyl product.

To 474.8 mg (1.93 mM) of 5,6-dihydroxy-2-methylisoindoline hydrobromide, 10 ml of ethyl acetate, 0.28 ml (2 mM) of triethylamine and 1.7 ml of N,O-bis(trimethylsilyl)acetamide were added, and the mixture was stirred for 1 hour. Insolubles were removed by filtration. The filtrate was added to the ethyl acetate solution of the 3-iodomethyl product prepared above, and the mixture was stirred for 30 minutes. Ethyl ether was added to the reaction solution thus obtained. Precipitates thereby formed were collected by filtration, and dried under reduced pressure to obtain 900 mg of benzyhydryl 7-benzylideneamino-3-[5,6-di(trimethylsilyloxy)-2-methyl-2-isoindolinium]methyl-3-cephem-4-carboxylate iodide.

EXAMPLE 4

7-Amino-3-(5,6-dihydroxy-2-methyl-2-isoindolinium)methyl-3-cephem-4-carboxylate hydrochloride 900 mg of benzyhydryl 7-benzylideneamino-3-[5,6-di(trimethylsilyloxy)-2-methyl-2-isoindolinium]methyl-3-cephem-4-carboxylate iodide as obtained in Example 3 was dissolved in 2.6 ml of 99% formic acid. Then, 1.62 ml of concentrated hydrochloric acid was added thereto, and the mixture was stirred for 1 hour. To this reaction solution, 48 ml of acetone was added, and precipitates were collected by filtration. The precipitates were dissolved in 5.8 ml of water, and then 100 ml of acetone was added thereto. Precipitates thereby formed were collected by filtration, and dried under reduced pressure to obtain 297 mg of 7-amino-3-(5,6-dihydroxy-2-methyl-2-isoindolinium)methyl-3-cephem-4-carboxylate hydrochloride. The melting point and the IR and NMR spectrum data of this product agreed to those of the compound obtained Example 2.

EXAMPLE 5

3-(5,6-dihydroxy-2-methyl-2-isoindolinium)methyl-7-phenylacetamido-3-cephem-4-carboxylate 973 mg (2 mM) of p-methoxybenzyl 3-chloromethyl-7-phenylacetamido-3-cephem-4-carboxylate was dissolved in a mixture comprising 20 ml of acetone and 20 ml of methylene chloride. Then, 900 mg (6 mM) of sodium iodide was added thereto, and the mixture was stirred for 1 hour. From the reaction solution thus obtained, the solvent was distilled off under reduced pressure, and ethyl acetate was added to the residue. The mixture was washed with a saturated sodium thiosulfate aqueous solution and then with a saturated sodium chloride aqueous solution, then dried over anhydrous sodium sulfate and filtered to obtain an ethyl acetate solution containing the 3-iodomethyl product.

590 mg (2.4 mM) of 5,6-dihydroxy-2-methylisoindoline hydrobromide was added to 12 ml of methylene chloride. Then, 0.35 ml (2.5 mM) of triethylamine and 2.37 ml of N,O-bis(trimethylsilyl)acetamide were added thereto, and the mixture was stirred for 1 hour. From the reaction solution thus obtained, the solvent was distilled off, and tetrahydrofuran was added to the residue. Insolubles were removed by filtration. The filtrate thus obtained was added to the ethyl acetate solution containing the 3-iodomethyl product prepared above, and the mixture was stirred for 30 minutes. This reaction solution was concentrated under reduced pressure to ¼. Then, isopropyl ether was added thereto, and precipitates thereby formed were collected by filtration. The precipitates were dissolved in 4.2 ml of 99% formic acid. Then, 2.1 ml of concentrated hydrochloric acid was added, and the mixture was stirred for 1 hour. The reaction solution thus obtained was poured into 200 ml of acetone. Precipitates thereby formed were collected by filtration, and dried under reduced pressure to obtain 495 mg of 3-(5,6-dihydroxy-2-methyl-2-isoindolinium)-methyl-7-phenylacetamido-3-cephem-4-carboxylate.

m.p.: 167–168° C. (decomposed)
IR(KBr)cm$^{-1}$: 1770, 1620, 1340
NMR(DMSO-d$_6$) δ ppm: 3.00(3H,br s), 3.20–3.90(4H,m),
4.00–4.90(6H,m), 5.00(1H,d,J=4.5 Hz),
5.52(1H,dd,J=4.5 and 9 Hz), 6.75(2H,s),
7.27(5H,s)

EXAMPLE 6

7-Amino-3-(5,6-dihydroxy-2-methyl-2-isoindolinium)methyl-3-cephem-4-carboxylate hydrochloride 495 mg (1 mM) of 3-(5,6-dihydroxy-2-methyl-2-isoindolinium)methyl-7-phenylacetamido-3-cephem-4-carboxylate was suspended in 12.5 ml of water, and the suspension was adjusted to pH 7.8 with a 4N triethylamine/ethanol solution. Then, 1 g of fixed penicillin-G-amidase (Bellingham-Manheim Company) was added thereto. While maintaining the mixture at pH 7.8 with a 4N triethylamine/ethanol solution at 20° C., the mixture was stirred for 1 hour. From the reaction solution thus obtained, the amidase was removed by filtration, and the filtrate was adjusted to pH 2.0. Insolubles thereby formed were removed by filtration. The filtrate was poured into 200 ml of acetone. Precipitates thereby formed were collected by filtration, and dried under reduced pressure to obtain 114 mg (yield: 27.5%) of 7-amino-3-(5,6-dihydroxy-2-methyl-2-isoindolinium)- methyl-3-cephem-4-carboxylate hydrochloride. The melting point and the IR and NMR spectrum data of this product agreed to those of the compound obtained in Example 2.

EXAMPLE 7 p-Methoxybenzyl 7-formamido-3-(5,6-dihydroxy-2-methyl-2-isoindolinium)methyl-3-cephem-4-carboxylate iodide 15.8 g (32.4 mM) of p-methoxybenzyl 7-formamido-3-iodomethyl-3-cephem-4-carboxylate was dissolved in 150 ml of N,N-dimethylformamide. To this solution, 5.46 g (33.1 mM) of 5,6-dihydroxy-2-methylisoindoline was added at −10° C., and the mixture was stirred at a temperature of from −10 to −5° C. for 2 hours. Then, the reaction solution was poured into 800 ml of ethyl ether. Precipitates were collected by filtration, washed with ethyl acetate, and dried to obtain 20.0 g (yield: 95%) of p-methoxybenzyl 7-formamido-3-(5,6-dihydroxy-2-methyl-2-isoindolinium)-methyl-3-cephem-4-carboxylate iodide.

IR(KBr)cm$^{-1}$: 1780, 1740, 1620, 1520
NMR(DMSO-d$_6$/D$_2$O) δ ppm: 3.08(3H,br s), 3.50–4.20(2H,m),
4.30–4.90(6H,m), 5.13(2H,s),
5.17(1H,d,J=4.5 Hz),
5.35(1H,d,J=4.5 Hz), 6.78(2H,s),
6.90(2H,d,J=9 Hz),
7.27(2H,d,J=9 Hz), 8.20(1H,s)

EXAMPLE 8

7-Amino-3-(5,6-dihydroxy-2-methyl-2-isoindolinium)methyl-3-cephem-4-carboxylate hydrochloride 31 g (47.5 mM) of p-methoxybenzyl 7-formamido-3-(5,6-dihydroxy-2-methyl-2-isoindolinium)-methyl-3-cephem-4-carboxylate iodide was dissolved in a solution comprising 31 ml of 99% formic acid and 31 ml of tetrahydrofuran. Under cooling with ice, 31 ml of concentrated hydrochloric acid was added to this solution, and the mixture was stirred at room temperature for 4.5 hours. The reaction solution was poured into 1.2 liter of acetone. Precipitates were collected by filtration, washed with acetone and dried to obtain 15.9 g (yield: 78%) of 7-amino-3-(5,6-dihydroxy-2-methyl-2-isoindolinium)methyl-3-cephem-4-carboxylate hydrochloride. The melting point and the IR and NMR spectrum data of this product agreed to those of the compound obtained in Example 2.

EXAMPLE 9

7-Amino-3-(5,6-dihydroxy-2-methyl-2-isoindolinium)methyl-3-cephem-4-carboxylate hydrochloride 300 mg (0.8 mM) of 7-amino-3-iodomethyl-3-cephem-4-carboxylic acid hydrochloride was suspended in 10 ml of acetonitrile, and dissolved by an addition of 0.75 ml (3.0 mM) of N,O-bis(trimethylsilyl)acetamide under cooling with ice. To this solution, 165 mg (1.0 mM) of 5,6-dihydroxy-2-methylisoindoline was added under cooling with ice, and the mixture was stirred for 30 minutes and further stirred at room temperature for 1 hour. The reaction solution was concentrated under reduced pressure. To the residue, 15 ml of methanol and 1 ml of water were added, and the mixture was stirred at room temperature for 15 minutes. After removing insolubles by filtration, the filtrate was concentrated under reduced pressure. To the residue, acetone was added. Precipitates thereby formed were collected by filtration, and dried to obtain 60 mg (yield: 18.6%) of 7-amino-3-(5,6-dihydroxy-2-methyl-2-isoindolinium)-methyl-3-cephem-4-carboxylate hydrochloride. The melting point and the IR and NMR spectrum data of this product agreed to those of the compound obtained in Example 2.

By using the compound of the present invention, cephalosporin derivatives expected to be useful as antibacterial agents, can efficiently be produced. Thus, the present invention contributes to the production of antibacterial agents.

What is claimed is:

1. A compound having the formula:

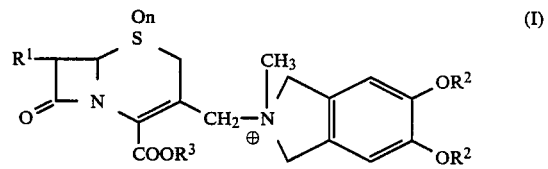

wherein R$^1$ is an amino group or a protected amino group having a protected group selected from the group consisting of benzylidene, phenylacetyl, formyl, tertbutoxycarbonyl and trityl, R$^2$ is a hydrogen atom or a protecting group for a hydroxyl group selected from the group consisting of acetyl and trimethylsilyl, R$^3$ represents negative charge, a hydrogen atom or a protecting group for a carboxyl group, and n is 0 or 1, and a salt thereof.

2. The compound according to claim 1, wherein R$^1$ is an amino group, a p-chlorobenzylideneamino group, a p-nitrobenzylideneamino group, a formylamino group, a tert-butoxycarbonylamino group, a chloroacetylamino group, a benzyloxycarbonylamino group, a tritylamino group, a benzylamino group, an α-naphthylideneamino group, a β-naphthylideneamino group, a phenylacetylamino group, a benzylideneamino group or a salicylideneamino group.

3. The compound according to claim 1, which is in the form of a solvate.

4. The compound according to claim 1, which is 7-amino-3-(5,6-dihydroxy-2-methyl-2-isoindolinium)-methyl-3-cephem-4-carboxylate or a salt thereof.

5. The compound according to claim 1, which is 7-amino-3-(5,6-dihydroxy-2-methyl-2-isoindolinium)-methyl-3-cephem-4-carboxylate hydrochloride or a solvate thereof.

6. The compound according to claim 1, which is 7-amino-3-(5,6-dihydroxy-2-methyl-2-isoindolinium)-methyl-3-cephem-4-carboxylate dihydrochloride or a solvate thereof.

7. The compound according to claim 1, which is p-methoxybenzyl 7-benzylideneamino-3-[5,6-di(trimethylsilyloxy)-2-methyl-2-isoindolinium]methyl-3-cephem-4-carboxylate iodide.

8. The compound according to claim 1, which is benzhydryl 7-benzylideneamino-3-[5,6-di(trimethylsilyloxy)-2-methyl-2-isoindolinium]methyl-3-cephem-4-carboxylate iodide.

9. The compound according to claim 1, which is 7-phenylacetamido-3-(5,6-dihydroxy-2-methyl-2-isoindolinium)methyl-3-cephem-4-carboxylate.

10. The compound according to claim 1, which is p-methoxybenzyl 7-formamido-3-(5,6-dihydroxy-2-methyl-2-isoindolinium)methyl-3-cephem-4-carboxylate iodide.

* * * * *